(12) United States Patent
Zhu

(10) Patent No.: US 9,510,836 B2
(45) Date of Patent: Dec. 6, 2016

(54) LIVING TISSUE LIGATION DEVICE

(71) Applicant: Jian Zhu, Guangdong (CN)

(72) Inventor: Jian Zhu, Guangdong (CN)

( * ) Notice: Subject to any disclaimer, the term of this patent is extended or adjusted under 35 U.S.C. 154(b) by 345 days.

(21) Appl. No.: 14/234,642

(22) PCT Filed: Nov. 12, 2012

(86) PCT No.: PCT/CN2012/084467
§ 371 (c)(1),
(2) Date: Jan. 24, 2014

(87) PCT Pub. No.: WO2013/067974
PCT Pub. Date: May 16, 2013

(65) Prior Publication Data
US 2014/0171973 A1 Jun. 19, 2014

(30) Foreign Application Priority Data
Nov. 11, 2011 (CN) .......................... 2011 1 0358591

(51) Int. Cl.
*A61B 17/122* (2006.01)
*A61B 17/128* (2006.01)
*A61B 17/29* (2006.01)

(52) U.S. Cl.
CPC ........... *A61B 17/122* (2013.01); *A61B 17/128* (2013.01); *A61B 17/1227* (2013.01); *A61B 17/1285* (2013.01); *A61B 2017/2905* (2013.01)

(58) Field of Classification Search
CPC . A61B 17/122; A61B 17/128; A61B 17/1285; A61B 17/12; A61B 17/1227; A61B 2017/12004

USPC ........ 606/139, 142, 143, 151, 157, 158, 219
See application file for complete search history.

(56) References Cited

U.S. PATENT DOCUMENTS

| | | | | |
|---|---|---|---|---|
| 5,766,189 | A * | 6/1998 | Matsuno | A61B 17/128 606/139 |
| 7,108,699 | B2 * | 9/2006 | Kobayashi | A61B 17/1285 606/142 |
| 7,494,461 | B2 * | 2/2009 | Wells | A61B 17/122 600/104 |
| 7,854,739 | B2 * | 12/2010 | Satake | A61B 17/1285 606/142 |
| 8,939,997 | B2 * | 1/2015 | Martinez | A61B 17/08 606/1 |
| 9,072,520 | B2 * | 7/2015 | Terada | A61B 17/1222 |
| 2002/0133178 | A1 * | 9/2002 | Muramatsu | A61B 17/1285 606/142 |
| 2003/0069592 | A1 * | 4/2003 | Adams | A61B 17/122 606/142 |
| 2004/0133228 | A1 * | 7/2004 | Bayer | A61B 17/00008 606/190 |

(Continued)

*Primary Examiner* — Todd E Manahan
*Assistant Examiner* — Charles Wei

(57) ABSTRACT

A living tissue ligation device, comprising a clamp (10), an operating device (20) and a conveying device (30); the clamp (10) comprising an elastic clip (11) and a tightening tube (12) to receive the elastic clip (11) therein; the operating device (20) comprise a handle (21) and a slider (22) capable of sliding on the handle (21); and the conveying device (30) comprises an outer connecting mechanism (31) and an inner connecting mechanism (32). The device can be widely used at various positions in the alimentary canal, can be repeatedly opened and closed, and is simple to operate.

16 Claims, 11 Drawing Sheets

(56) References Cited

U.S. PATENT DOCUMENTS

| | | | |
|---|---|---|---|
| 2005/0187574 A1* | 8/2005 | Senzaki | A61M 25/1002 606/194 |
| 2008/0306491 A1* | 12/2008 | Cohen | A61B 17/122 606/142 |
| 2011/0046651 A1* | 2/2011 | Cohen | A61B 17/1227 606/157 |
| 2012/0109160 A1* | 5/2012 | Martinez | A61B 17/08 606/142 |
| 2013/0123818 A1* | 5/2013 | Li | A61B 17/122 606/157 |
| 2015/0190136 A1* | 7/2015 | Cohen | A61B 17/122 606/143 |

* cited by examiner

A-A

C-C

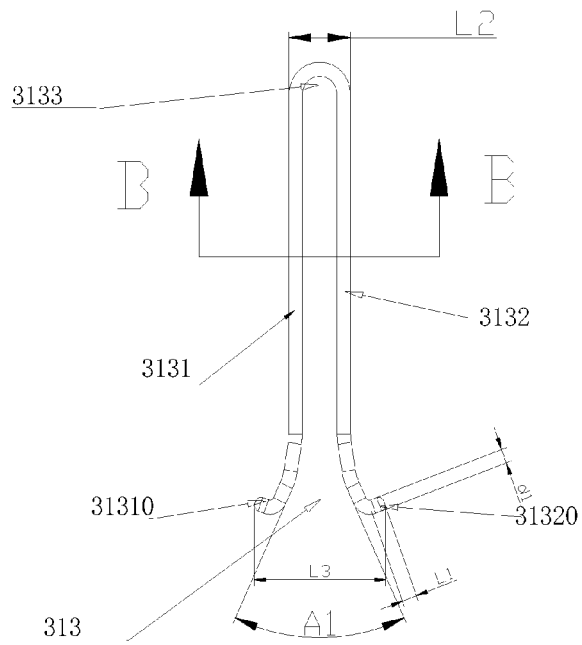
FIG. 11
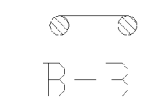
FIG. 11a
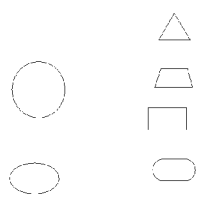
FIG. 11b
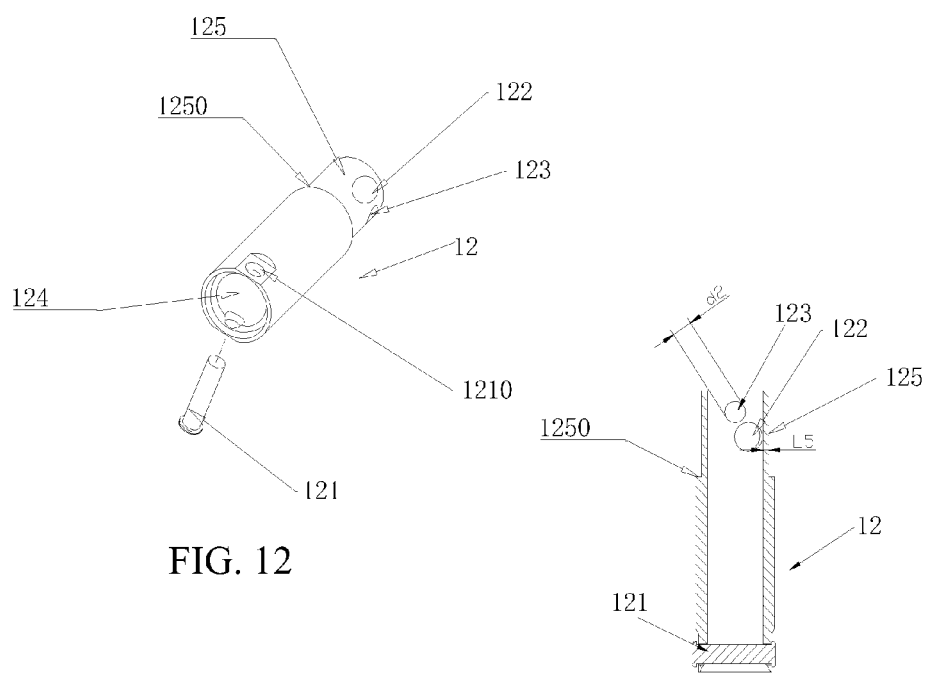
FIG. 12
FIG. 12a

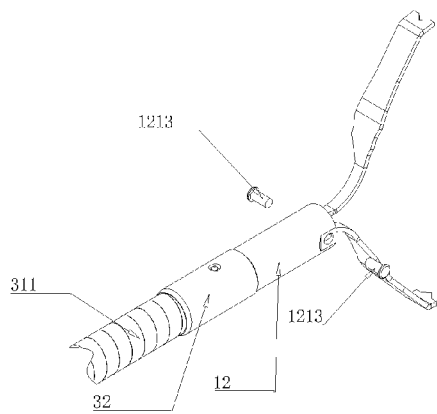
FIG. 20b
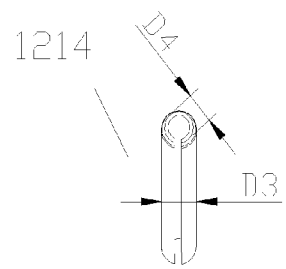
FIG. 20c
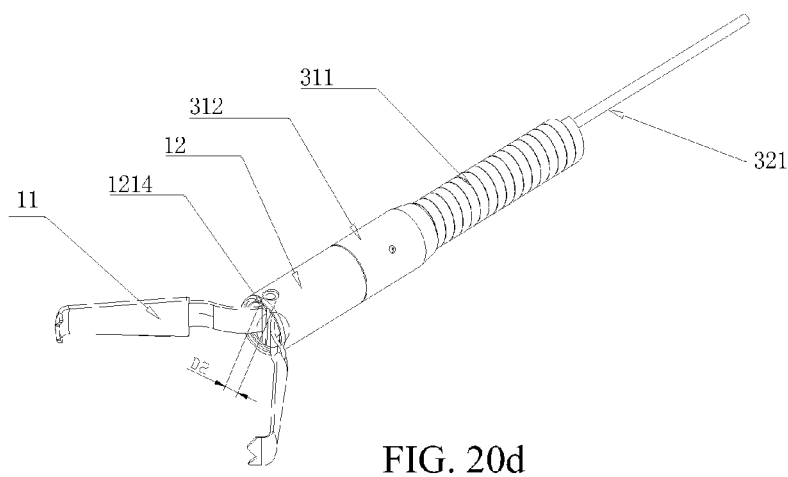
FIG. 20d
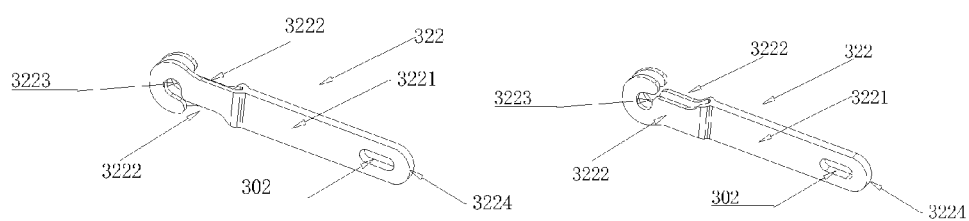
FIG. 21a
FIG. 21b

LIVING TISSUE LIGATION DEVICE

FIELD OF THE INVENTION

The present invention relates to a living tissue ligation device, mainly used in digestive diseases subjects, especially for treatment with colonoscopy and endoscope, and non-variceal active bleeding treatment under endoscopy, which belongs to the technical field of micro-invasive medical devices.

BACKGROUND OF THE INVENTION

As the endoscope was available for more than 50 years, and has gone through from disease diagnosis to disease treatment, the endoscope is so effective and reliable at treating diseases. The stomach and intestines of an organism bleed due to various diseases, accidental damage or damage caused by the endoscopic treatment. As for treating active bleeding, it usually uses drug spraying, high-frequency electric, laser, or mechanical hemostatic method using a hemostatic clamp. The mechanical hemostatic method using hemostatic clip at treating non-variceal active bleeding has reliable therapeutic efficacy, which is accepted by doctors and patients. Furthermore, mechanical clamp hemostatic method could be used in treating intestinal mucosal injury to heal the wounds, and closing the alimentary tract, avoiding open surgery.

Clinically relevant hemostatic clamps could divide into three types.

One type of hemostatic clamp is formed by separated clip and device. The clip is one-time used, and the device could be reused. When the clip is released, the doctor has to assemble another new clip and device, which would result in a complex operation. Pull a handle to one end of the device to open or fold the clip, which is not easy to control the clip and makes the clip folded before being used, and the clip could not be opened again once it is folded. Once the clip is released at a wrong position, it need to remove the clip by an equipment, and assemble another clip again and send it to the lesion location and re-released it. The length of the clip is approximately 10-12 mm after being released, and disinfecting the device is required to the surgery, repeated disinfection will increase the risk of infection in surgery.

The second type of clamp has a clip and a device integrated together, and could not be repeatedly opened. The clip is to be opened or folded by pulling a handle to one end of the device, as the first type of hemostatic clip acts, which is not easy to control the clip and makes the clip folded before being used, and the clip could not be opened again once it is folded. Once the clip is released at a wrong position, it need to remove the clip by equipment, and assemble another clamp again to the lesion location and clamp the injured part. But this clip is without assembly on the clamp, which makes the operation more convenient than the first type. After releasing the clip length is approximately 10-12 mm.

The third type of clamp could be repeated opened and folded, and the clip and the device are integrated together, to be positioned repeatedly, compared with the previous two types of clamps, it is more advanced but its structure is more complex, that is pushing the sliding handle to open the clip, and pulling the slide handle to fold the clip, which make the opening and closing action in the opposite direction, and it is easy to misuse. After the release the clip, the clip length is about 15.5 mm with the tail having spiny protrusion, which is not suitable for putting into small spaces, such as the esophagus, and there will be the risk of causing esophagus perforation.

Clinicians fully expect to one type of one-time used living tissue ligation device having characteristics that make it repeat-positioning, easy to operate, could release shorter smooth clip tail. Repeat positioning feature helps physicians to observe whether the clamping position is accurate or not, and physician could observe the clamp position through the endoscope display screen to judge whether the clip is released to the accurate position, to make a desired effect, if yes, then he releases the clip, if not, the physician opens the clip again to clamp the accurate living tissue, to ensure that the clamping position is accurate and effective. The opening and closing action of the clamp are in the opposite direction and easy to operate. The clip length is shorter and the clip has rounded end, which allows for applying in more digestive tracts, and also avoid the clip damaging the digestive tract owing to its long tail and sharp end.

SUMMARY OF THE INVENTION

The purpose of the present invention is to provide a living tissue ligation device fo single use, having a clamp and a device which are integrated design, with the clamp being locatable, and the length (about 12-13 mm) of the clamp is shorter after being released.

In order to achieve the above purpose, the present invention provides the following technical solution:

A living tissue ligation device, characterized by including a clamp, an operating unit, and a conveying unit; the clamp including elastic clips and a tightening tube to receive the elastic clip therein; the operating unit comprising a handle and a slider sliding on the handle; and the conveying unit comprising an outer connecting assembly and an inner connecting assembly; wherein the outer connecting assembly includes a spring tube, a connecting head, and a connecting rod; one end of the spring tube is connected to the handle, the other end of the spring tube is connected to one end of the connecting head, the other end of the connecting head is coupled to one end of the tightening tube via the connecting rod, and a connecting part of the connecting rod is disengaged from holes or grooves under a certain pull force, to make the connecting head disengage from the tightening tube; the inner connecting assembly which runs through the outer connecting assembly comprises a shaft, a connector and a joint stick; one end of the shaft is connected to the slider of the operating unit by a guiding bar, and the shaft is pulled by the slider; the other end of the shaft is connected to a near end of the connector; a far end of the connector is connected to one end of the elastic clip via the joint stick, and the far end of the connector is deformed under a certain pull force, to disengage from the end of the elastic clip; the connecting rod is pulled by the connector, and the connecting part of the connecting rod is disengaged from the holes or the grooves under the pull force.

Preferably, the connecting rod which is formed by bending a single piece of material includes two extended arms and a traction part which is arranged between two extended arms; at least one said extended arm has a free end having a wing formed thereon to engage with the hole or the groove correspondingly.

Preferably, the connecting rod which is formed by bending a single piece of material includes at least one extended arm and a traction part which is connected to the bottom of the extended arm; the extended arm has a free end having a wing formed thereon to engage with the holes or the grooves correspondingly.

Preferably, the connector includes a thin bar and a notch part connected to one end of the thin bar, the other end of the thin bar is connected to one end of the shaft, a free end of the notch part forms hooks, which form a first connecting hole to engage with the joint stick, a second connecting hole is formed at the bottom of the elastic clip to engage with the joint stick, and the joint stick runs through the first connecting hole and the second connecting hole, to make the elastic clip connect to the connector; the hooks are deformed under a certain pull force to disengage from the elastic clip.

Preferably, the notch part comprises two notch portions; each notch potion has a free end to form a hook, which forms a first connecting hole to engage with the joint stick.

Preferably, the thickness of the end of the thin bar is greater than the diameter of the shaft, and the thin bar has a contact portion at the point where the thin bar meets the shaft, when the shaft is pulled under a certain pull force, the contact portion is against the traction part of the connecting rod to make the wings of the connecting rod disengage from the holes or grooves.

Preferably, a divider slot is formed on one end of the connector along the end diameter, and a mounting hole is formed at the bottom of the divider slot to communicate the divider slot, the joint stick is locked in the mounting hole through the divider slot; the connector consists of elastic material.

Preferably, one end of the connector is a cylinder, a through-groove is formed on the wall of the cylinder along the axial direction, and the extended arm is through the through-groove to make the traction part arranged in the through-groove; a contact portion is formed on the connector, and when the shaft is pulled under a certain pull force, the contact portion is pressed against the traction part to make the wings of the connecting rod disengage from the holes or grooves.

Preferably, the elastic clip has an arm part n and an outer part connected to the arm part to form a connection; the diameter of the outer part is larger than that of the arm part to make the connection form a stopper, and stopper is against one end of the tightening tube when the elastic clips are received in the tightening tube in a certain position.

Preferably, a lug is formed on one end of the elastic clip; hanging holes are formed on an inner wall of the tightening tube, when the elastic clips are disengaged from the connector, each lug is locked in the hanging hole to prevent from the elastic clip being disengaged from the tightening tube.

Preferably, a curved base is formed at the bottom of the elastic clip of the clamp, a concave is formed on one end of the connector to match the curved base, with the curved base being received in the concave, and the joint stick being locked in the concave correspondingly, and the connector consists of elastic material, the concave is deformed under a certain pull force to disengage from the curved base and the joint stick.

Preferably, a separated member is arranged on one end of the tightening tube to separate the elastic clips and prevent the elastic clips from disengaging from the tightening tube.

Preferably, the joint stick is a pin.

Preferably, the joint stick consists of metal material or high strength nonmetallic material, so that the joint stick is without deformation when the connector is under a certain pull force.

The living tissue ligation device mainly includes two parts: a clamp and a soft and spindly conveying unit, the clamp is mounted on the front end of the conveying unit, and the clip of the clamp could be pushed or pulled by the shaft to open, fold or release. The clip head and the conveying unit are both for single use without sterilization, which avoids the risk of cross infections, and the clamp could be repetitive positioning. When the clamp clamps the living tissue, the physician could observe the clamp position through the endoscope to judge whether the clip is released to the accurate position, to make a desired effect, if the clamping position is not he expects, the physician could push the handle slowly to make the clip open, and clamps the accurate living tissue he expects, then pulls the handle until it could not be pulled, and to head a clicking sound, so that the clamp and the conveying unit are separated owing to the certain pull force, to achieve that the clip is released and remains in the digestive tract of an organism to ligate the affected part and make it stop bleeding.

The present invention applies the above technical solution, to provide the physician with a living tissue ligation device, which could be widely used at various positions in the digestive tract, with repeatedly opening and closing, and is simple to be operated, so as to save the surgery time and reduce the surgery risk greatly.

BRIEF DESCRIPTION OF THE DRAWINGS

FIG. 11 is a schematic diagram showing a preferred connecting rod of the living tissue ligation device according to an embodiment of the present invention;

FIG. 11a is a schematic diagram of part B-B shown in FIG. 11;

FIG. 11b is a schematic diagram showing other types of the connecting rod of the living tissue ligation device according to an embodiment of the present invention;

FIG. 12 is a schematic diagram showing a preferred tightening tube of the living tissue ligation device according to an embodiment of the present invention;

FIG. 12a is a sectional view showing the tightening tube shown in FIG. 12;

FIG. 19b is a schematic diagram showing the bending stop arm of the tightening tube shown in FIG. 19a;

FIG. 19c is a schematic diagram showing the tightening tube with the clip mounted therein shown in FIG. 19a;

FIG. 20b is a schematic diagram showing the clip, the connecting head, and the spring tube of the living tissue ligation device according to another embodiment of the present invention, and showing another stop member thereof;

FIG. 20c is a schematic diagram showing the stop member according to another embodiment of the present invention;

FIG. 20d is a use state diagram showing the stop member of FIG. 20c;

FIGS. 21a and 21b are schematic diagrams showing the connectors of the living tissue ligation device according to another two embodiments of the present invention;

FIG. 22b is a schematic diagram of part B-B shown in FIG. 22a;

FIG. 22c is a schematic diagram of part A-A shown in FIG. 22a;

FIG. 22d is a stereogram showing the connector of FIG. 22a;

DETAILED DESCRIPTION OF ILLUSTRATED EMBODIMENTS

Figure 1:
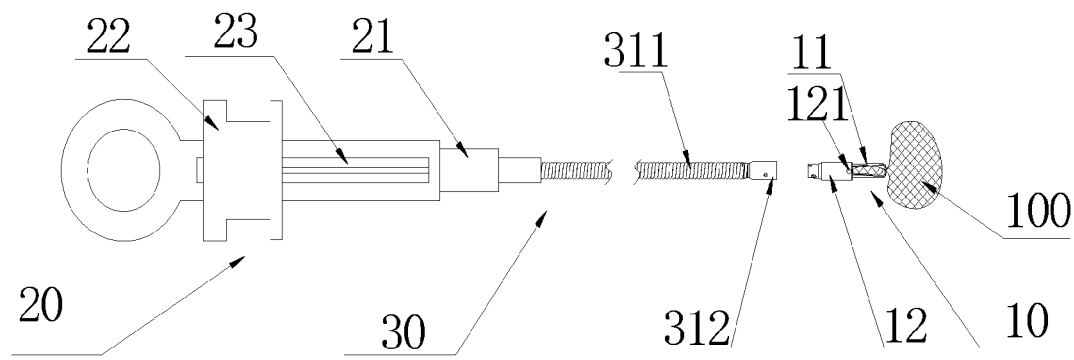
FIG. 1 is a schematic diagram showing the living tissue ligation device according to an embodiment of the present invention, with the elastic clip of the clamp ligating the living tissue.
Figure 2:
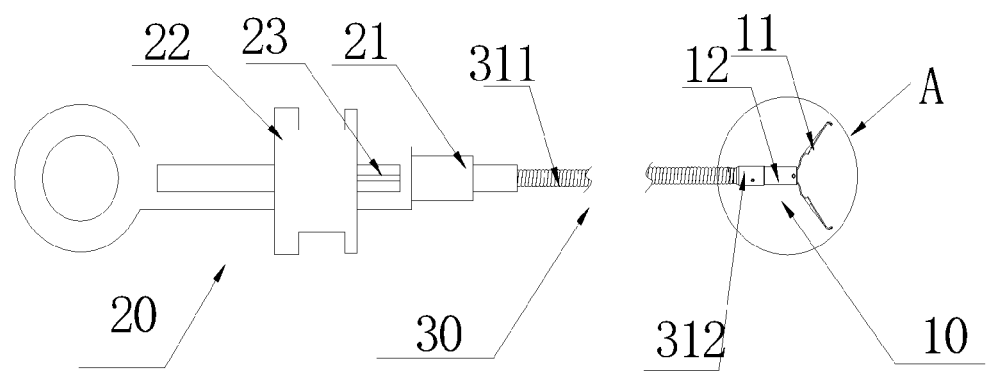
FIG. 2 is a schematic diagram showing the living tissue ligation device according to an embodiment of the present invention, with the elastic clip of the clamp in opening state.
Figure 2A:
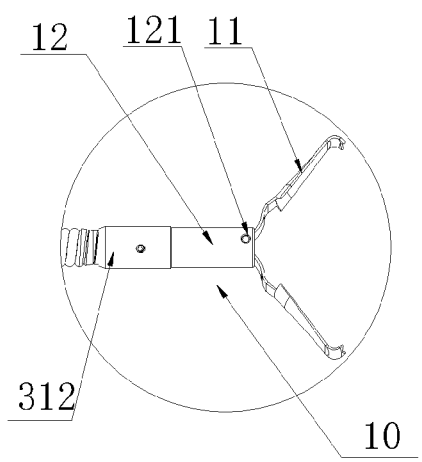
FIG. 2a is a partial enlarge diagram of part A shown in FIG. 2.

FIGS. 1-15 and 16 demonstrate the living tissue ligation device and its components according to a preferred embodiment of the present invention.

The living tissue ligation device includes a clamp 10, an operating unit 20, and a conveying unit 30.

The clamp 10 includes elastic clips 11 and a tightening tube 12 to receive the elastic clips 11 therein. The operating unit 20 includes a handle 21 and a slider 22 sliding on the handle. The conveying unit 30 includes an outer connecting assembly 31 and an inner connecting assembly 32.

The outer connecting assembly 31 includes a spring tube 311, a connecting head 312, and a connecting rod 313. The near end of the spring tube 311 is connected the handle 21, the far end of the spring tube 311 is connected to the near end of the connecting head 312, the far end of the connecting head 312 is coupled to the near end of the tightening tube 12 via the connecting rod 313. A connecting part of the connecting rod 313 is disengaged from holes or grooves correspondingly under a certain pull force, so that the connecting head 312 is disengage from the tightening tube 12. The above force is produced by the following connector 322.

The inner connecting assembly 32 includes a shaft 321, a connector 322 and a joint stick 323, and runs through the outer connecting assembly 21. The near end 3211 of the shaft 321 is connected to the slider 22 of the operating unit 20 via a guiding bar 23, and is pulled by the slider 22. The far end 3212 of the shaft 321 is connected to the near end 3221 of the connector 322; the far end 3222 of the connector 322 is connected to the near end 111 of the elastic clip 11 via a joint stick 323, and the far end 3222 of the connector 322 is deformed under a certain pull force, so as to disengage from the near end 111 of the elastic clip 11.

The above living tissue ligation device mainly includes two parts: a clamp 10 and a soft and spindly conveying unit 30. The clamp 10 is mounted on the front end of the conveying unit 30 in advance, and this mounting relationship could be destroyed under a certain pull force, so that the clamp 10 is separated from the conveying unit 30 and the clamp 10 is released. Before the certain pull force is achieved, the elastic clips 11 of the clamp 10 could be pushed or pulled by the shaft 321 (which is pulled by the slider 22 of the operating unit), so that the elastic clips 11 is controlled to open or fold many times, and the clamp 10 processes the function of repetitive positioning.

When use the living tissue ligation device through the endoscope to clamp the living tissue, the physician firstly pulls the handle 21 to fold the elastic clips 11 slowly, and this step calls "pre-clamp". Then, the physician could observe the affected part through the endoscope to judge whether the clamping is to achieve the desired effect, so to judge whether the clamp 10 is released. If the clamping position is not he expects after observation, the physician could push the handle 21 slowly to make the elastic clips 11 open, and clamps the living tissue in the digestive tract where he expects again until accurate living tissue is clamped after observation, then pulls the handle until the handle could not be pulled and is locked up, and a clicking sound is produced, so that the clamp 10 and the conveying unit 30 are separated owing to the certain pull force, and this step calls "release". Therefore, the clamp 10 clamps the living tissue of the digestive tract, and remains in the digestive tract of an organism to ligate the affected part and make it stop bleeding. Furthermore, the living tissue ligation device is not limited to be used for the living tissue of the digestive tract.

Below are the descriptions of the outer connecting assembly 31 and the tightening tube 12.

The outer connecting assembly 31 includes a spring tube 311, a connecting head 312, and a connecting rod 313.

The spring tube 311 is mounted on the end with a chamfer 3123 of the connecting head 312 by the solder crimp, that is, the near end of the connecting head 312 is connected to the far end of the spring tube 311. The spring tube 311 is made of wrapped spring wire and has sufficient flexibility, and is capable of withstanding big pressure and certain full force.

The connecting rod 313 includes two extended arms 3131 and 3132, and a traction part 3133 which is connected to the bottom of the extended arms. The tops of two extended arms 3131 and 3132 provides wings 31310 and 31320, which match and insert into the side holes 3121 of the connecting head 312 and the side holes 123 of the tightening tube 12 correspondingly. The wings 31310 and 31320 are capable of being deformed under a certain pull force to disengage from the side holes 123 and 3121 correspondingly, so that the connecting head 312 and the tightening tube 12 are without connection. The traction part 3133 is the pressure point of the pull force, and the following descriptions would show that the contact portion 3224 of the connector 322 is against the traction part 3133 to move, so as to achieve the disengagement of the wings. In this embodiment, the section of the extended arm is as shown in FIG. 11a, further in other embodiments, all kinds of extended arms with the sections shown in FIG. 11b are applicable in the present invention.

Figure 13:
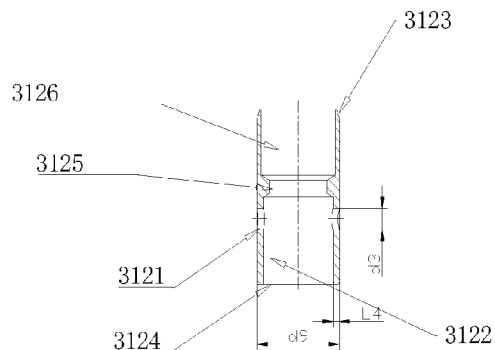
FIG. 13 is a schematic diagram showing a preferred connecting head of the living tissue ligation device according to an embodiment of the present invention.

Referring to FIGS. 12 and 13, the connecting head 312 includes a linking hole 3122 to receive the tightening tube 12 therein, and two side holes 3121 to have the connecting part of the connecting rod 313 to lock therein. Two side holes 123 are formed on the linking part 125 of the tightening tube 12, and the wings of the connecting rod 313 are inserted into the side holes 123 to make the connecting rod 313 mount on the tightening tube 12. Two side holes 3121 are formed on the coupling position of the connecting head 312, and the linking part 125 of the tightening tube 12 which is equipped with the connecting rod 313 is inserted into the linking hole 3122 of the connecting head 312, and two wings of the connecting rod 313 are pressed towards each other. Then, the tightening tube 12 is to be turned to make the sides hole 3121 of the connecting head 312 align at the side hole 123 of the tightening tube 12, at this point, the pressed wings bounces to insert into the sides hole 3121 of the connecting head 312. At this moment, the linking end face 1250 of the tightening tube 12 contacts the far end face 3124 (and the separated step 3125) of the connecting head 312, the tightening tube 12 is mounted on the connecting head 312 in axial direction by the wings of the connecting rod 313. The other parts of the connecting head 312 are shown in FIG. 13, such as the coupling hole 3126 of the spring tube.

The maximum width of the traction part 3133 of the connecting rod 313 is L2=1.15 mm, which is smaller than the inside diameter of the spring tube 311 which is d10=1.2 mm, and the traction part could be received in the spring tube 311, the shape of the cross section of the connecting rod 313 could be round, rectangle, square or oval, etc, but the diameter of this cross section is best limited to about 0.2-0.3 mm, and shall not limit the movement of the shaft 321, and the preferred cross section of the connecting rod should be a round with 0.2 mm diameter. The maximum space L3 between two wings of the connecting rod 313 is bigger than the outer diameter d9 of the connecting head 312, and the length L1=0.04 mm of the wing is smaller than the sum of the side wall thickness L5=0.2 and the side wall thickness L4=0.3 mm of the connector 322, so as to prevent from the projecting of the wings to against the operation of the physician; and the length of the wing is longer than 0.25 mm, to prevent the connecting rod 313 from disengagement to separate the clamp 10 and the conveying unit 30.

If the wings of the connecting rod 313 are not disengaged from the side holes, the connecting head 312 cannot be separated from the tightening tube 12; otherwise, if the wings of the connecting rod 313 are disengaged from the side holes of both the tightening tube 12 and the connecting head 312, the tightening tube 12 and the connecting head 312 are loose in the axis direction, so that the tightening tube 12 is separated from the connecting head 312.

Below are the descriptions of the inner connecting assembly and the clamp.

The inner connecting assembly includes a shaft 321, a connector 322, and a joint stick 323. The near end 3221 of the connector 322 is mounted on the shaft 321. The far end 3222 of the connector 322 is connected to the near end (the bottom end) of the elastic clip 11 via the joint stick 323, the structures are described in detail below.

Referring to FIGS. 5-10, the connector 322 includes a thin bar 3221 and a notch part 3222 connected to the far end of the thin bar 3221.

The near end of the thin bar 3221 is connected to the far end of the shaft 321 by laser welding, high-frequency welding, hinge joint, or other connection ways, which connection could afford certain separating force without destruction. The thickness which is 1.1 mm of the near end of the thin bar 3221 is greater than the diameter of the shaft 321, the inner diameter of the spring tube 311 is 1.2 mm, which occupies most of the inner hole of the spring tube 311, and the thin bar has a contact portion 3224 at the point where the thin bar connect to the shaft, when the shaft 321 is pulled under a certain pull force, the contact portion 3224 is against the traction part 3133 of the connecting rod 313 to make the wings of the connecting rod disengage from the holes or grooves correspondingly.

Figure 16A:
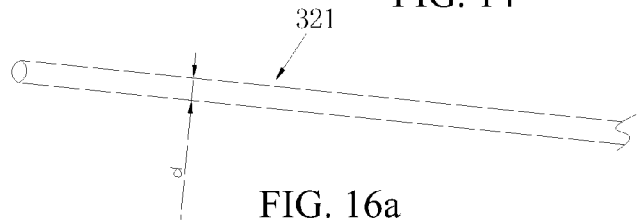
FIGS. 16a, 16b and 16c are schematic diagrams showing preferred embodiments of the shaft of the living tissue ligation device according to the present invention.
Figure 16B:
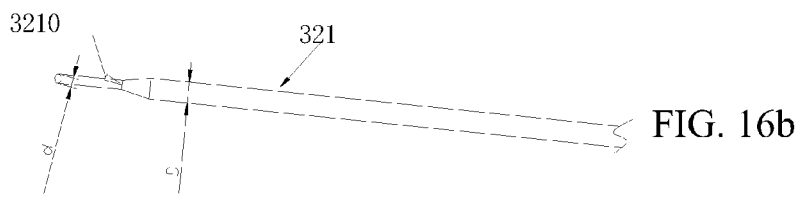
Figure 16C:
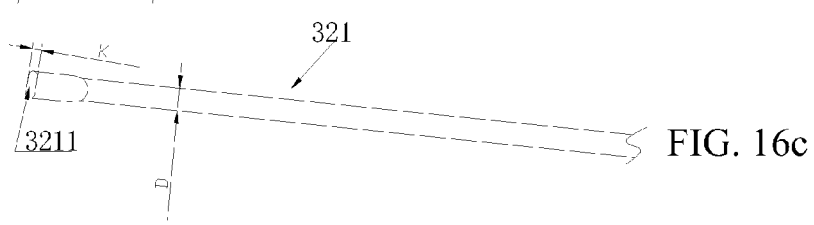

The shaft 321 could be the single metal wire or made by twisting several metal wires (as shown in FIG. 16a), referring to the preferred solution shown in FIG. 16c, the shaft 321 is made of an single steel wire (the diameter is 0.2 mm-1.1 mm), the front end of the shaft is flatten to be have 0.3 mm thick (the front end whose diameter is smaller than or equal to 0.3 mm does not need to be flatten or fined, the front end whose diameter is bigger than 0.6 mm needs fining process, the front end whose diameter is between 0.4-0.6 mm is flatten to be 0.3 mm or fined to be 0.3 mm), to form a flatten end 3211, which makes the shaft pass near the connecting rod 313 smoothly. In other embodiments of the present invention, the flatten end of the shaft 321 could be connected to the connector 322, to obtain better stable laser welding. The whole steel wire whose diameter is 0.3 mm or the steel wire with the front end being fined with 0.3 mm diameter could be employed, for (referring to FIGS. 8-10 and 16b, showing the thin end 3210), in favor of smooth movement.

The thin bar 3221 which is about 1.1 mm wide and 0.2-0.3 mm thick, could move in the spring tube 311 in axis direction freely, and the thin bar could come in all shapes, the premise is that the thin bar could be limited in a circle region with 1.1 mm-1.2 mm diameter, so as to move freely in the spring tube 311 without remain big gap between the thin bar and the inner hole of the spring tube. Off course, the size of the thin bar could change based on the actual requirement, as long as the free movement is achieved and the gap is not too big.

A free end of the notch part 3222 forms hooks, which form a first connecting hole 3223 to engaged with the joint stick. The elastic clips 11 has a structure of two plates, whose bottom provides two second connecting hole 117 to engaged with the joint stick 323. The joint stick 323 runs through the first connecting hole 3223 and the second connecting hole 117, so that the elastic clips 11 are connected to the connector 322. The hooks of the notch part could be deformed or broken when is applied on a certain pull force.

As for the notch part, in this embodiment, the notch part 3222 includes two notch portions 32221 and 32222, each notch portion has a free end to form a hook, which forms a first connecting hole 3223 to engaged with the joint stick 323. The hooks of the notch portions 32221 and 32222 are arranged in opposite direction. In other embodiment of the present invention, two hooks could be arranged in the same direction as shown in FIG. 43, or employ other suitable arrangement.

Figure 10:
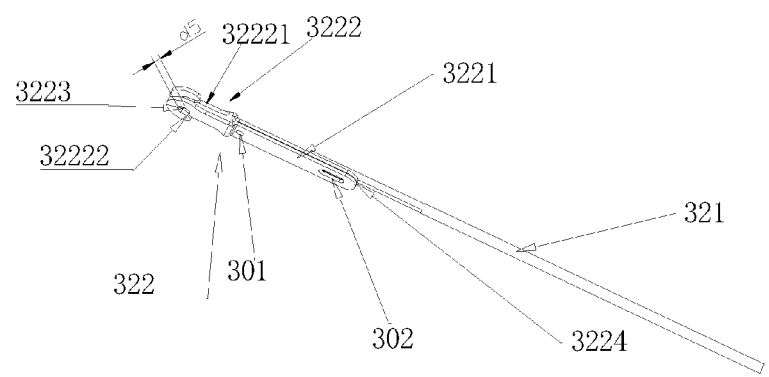
FIG. 10 is a schematic diagram showing the shaft connecting to the connector of the living tissue ligation device according to an embodiment of the present invention.
Figure 24:
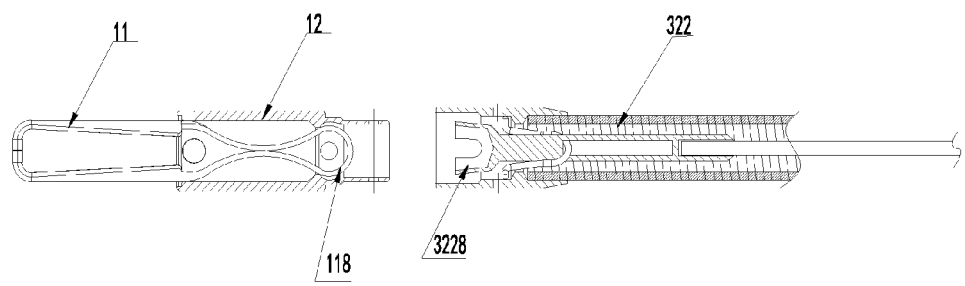
FIG. 24 is a schematic diagram showing the living tissue ligation device according the embodiment of the present invention, with the clamp being in folded state.

Specifically, firstly, the near end of each notch portion of the connector is connected to each other by welding the welding holes 301 (as shown in FIG. 10); or the near ends could be without welding holes, and two notch portion are connected to each other by laser welding or resistance welding, and the notch part could be without any welding or connection to make the far end of the connector be a free end (because the near end of the connector is connected to the shaft by welding); or two notch portions arranged on the far end of the connector are molded in one body without welding the welding holes, as shown in FIG. 24. Secondly, two notch portions 32221 and 32222 are separated to form a gap therebetween, then two elastic clips 11 are folded to insert into the gap or two notch portions block the near ends of two elastic clips 11, to prevent the lug 116 of each elastic clip 11 from locking in the hanging hole 122 of the tightening tube 12 in advance, when two elastic clips 11 are folded, to make the elastic clips could not be opened again. Thirdly, each second connecting hole 117 at the bottom of each elastic clip 11 is to align at the first connecting hole 3223, and then the joint stick 323 is inserted into the first connecting hole and the second connecting hole, to make the elastic clips 11 connect to the connector 322, and the shaft 321 is connected to the elastic clips 11 via the connector 322.

Figure 3:
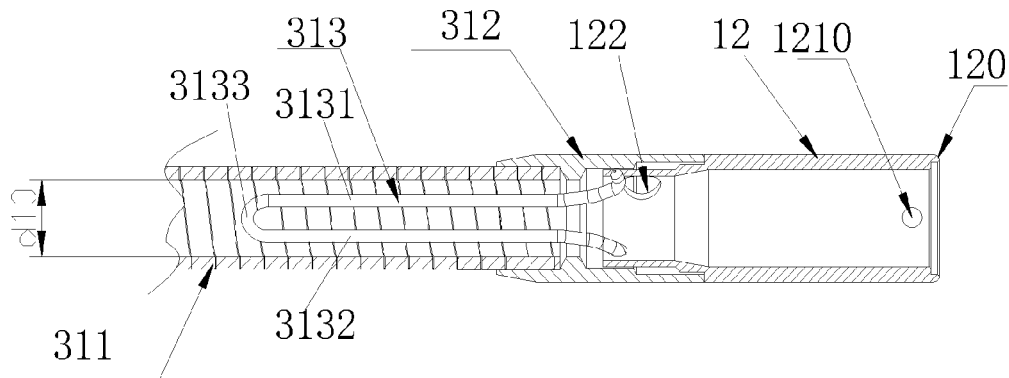
FIG. 3 is a sectional view showing the outer connecting assembly connecting to the tightening tube of the clamp of the living tissue ligation device according to an embodiment of the present invention.
Figure 4:
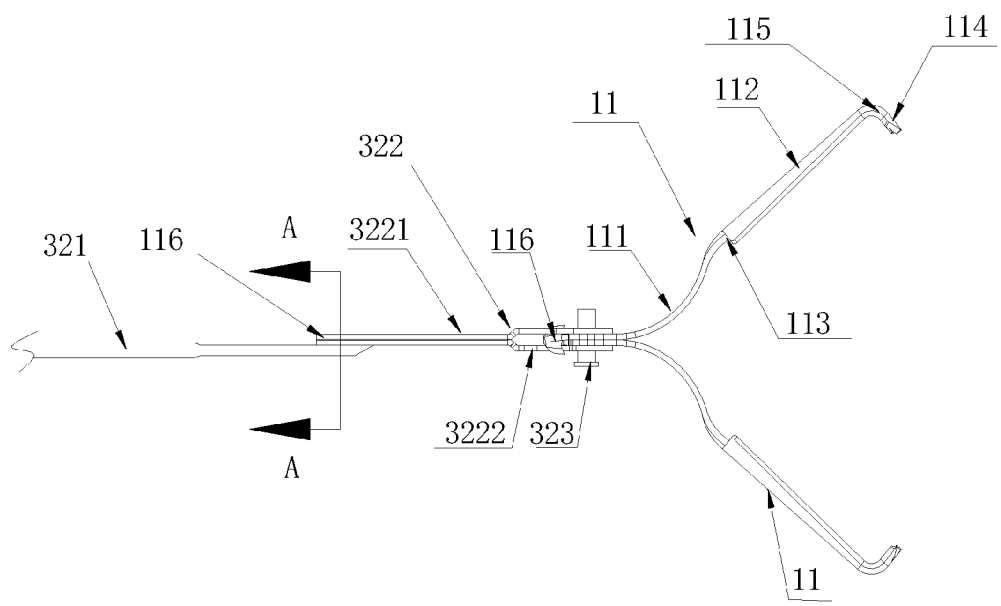
FIG. 4 is a sectional view showing the inner connecting assembly connecting to the tightening tube of the clamp of the living tissue ligation device according to an embodiment of the present invention.
Figure 4A:
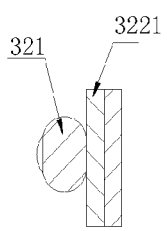
FIG. 4a is a schematic diagram of part A-A shown in FIG. 4.
Figure 6A:
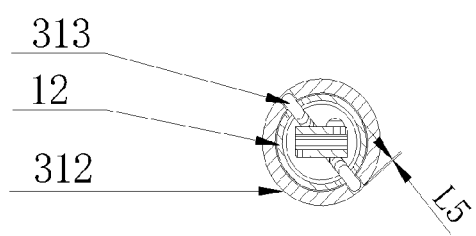
FIG. 6a is a schematic diagram of part C-C shown in FIG. 6.
Figure 5:
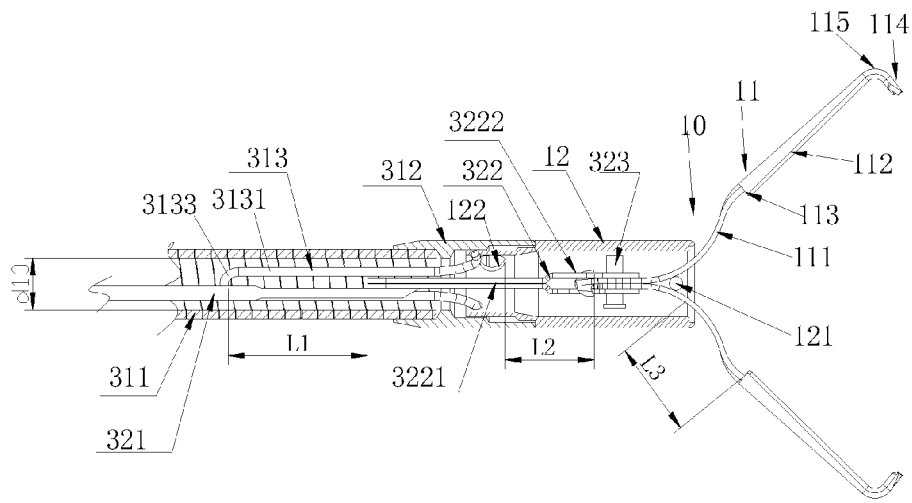
FIG. 5 is a sectional view showing the device assembled by components shown in FIGS. 3 and 4, with the elastic clip being in opening state.
Figure 6:
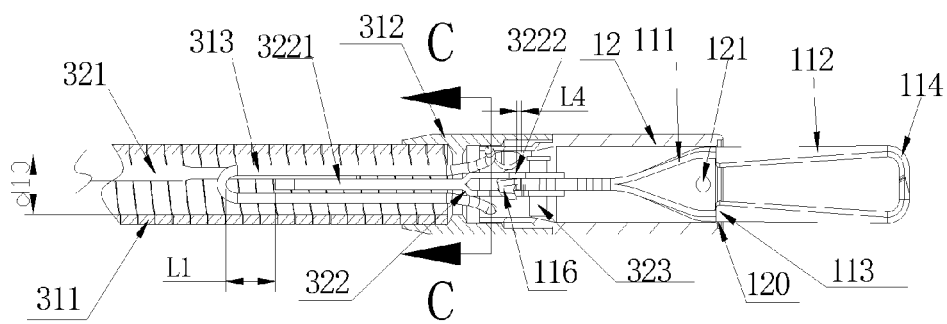
FIG. 6 is a sectional view showing the device assembled by components shown in FIGS. 3 and 4, with the elastic clip being in closing state.
Figure 7:
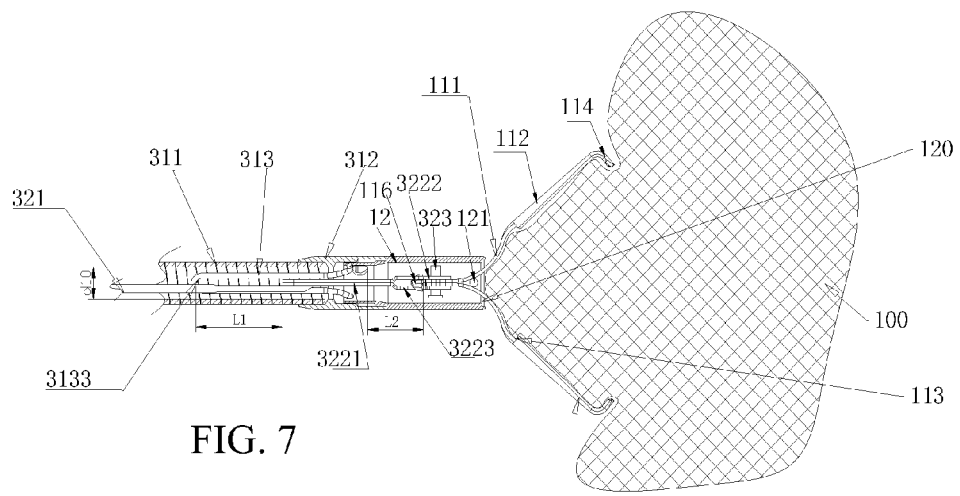
FIG. 7 is a schematic diagram showing the living tissue ligation device ready to clamp the living tissue, and showing a clamp and a conveying unit according to an embodiment of the present invention.
Figure 8:
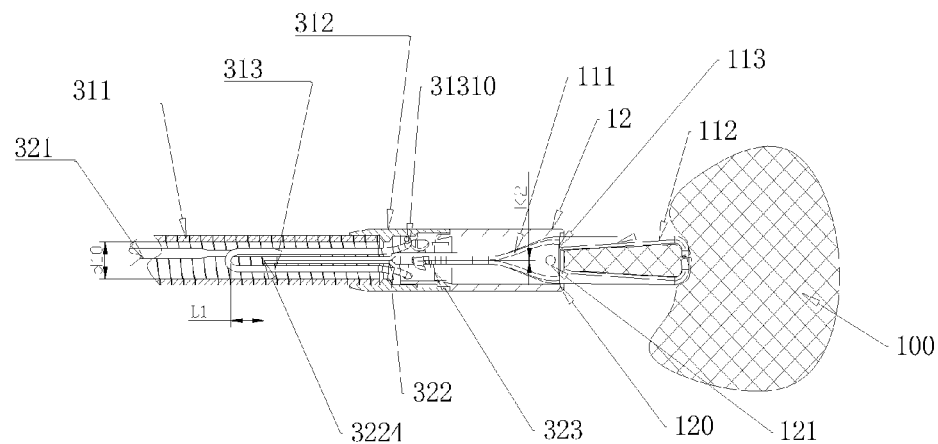
FIG. 8 is a schematic diagram showing the living tissue ligation device when clamping the living tissue, and showing a clamp and a conveying unit according to an embodiment of the present invention.
Figure 9:
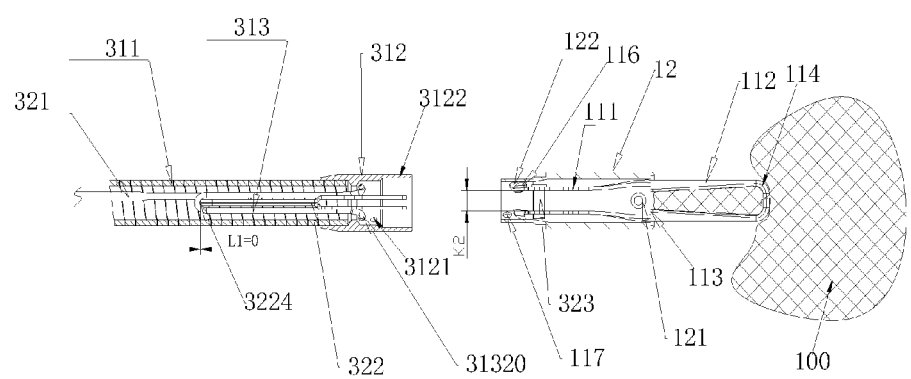
FIG. 9 is a schematic diagram showing the living tissue ligation device when the clamping action is finished, with the clamp and a conveying are separated according to an embodiment of the present invention.
Figure 15:
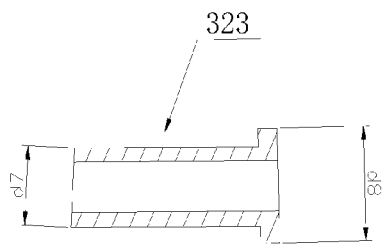
FIG. 15 is a schematic diagram showing a preferred joint stick of the living tissue ligation device according to an embodiment of the present invention.

Referring to FIGS. 3, 5 and 15, the joint stick 323 is a pin. In other embodiment, the joint stick 323 could be a tube, or with other shape capable of connecting to the connector and the elastic clips in prior art. The joint stick 323 is make of metal material or high strength nonmetallic material, so that the joint stick is without deformation when under a certain pull force, that is, when the notch part 3222 of the connector 322 is deformed, the joint stick 323 remains intact.

The detailed structure of the clamp is described below.

As described above, the clamp 10 includes elastic clips 11 and a tightening tube 12 to receive the elastic clips 11 therein.

The elastic clip 11 is made of elastic material, which are SUS301, SUS631, SUS304, etc, or any material with high elasticity, strength, and hardness, such as polymer material PEEK, plate, or strip with shape of round, rectangular, square, or ellipse cross section, etc; and the diameter of this cross section is best limited to about 0.2-0.3 mm, and shall not affect the movement of the shaft 321, and the preferred cross section of the elastic clip should be a round with 0.2 mm diameter.

Figure 14:
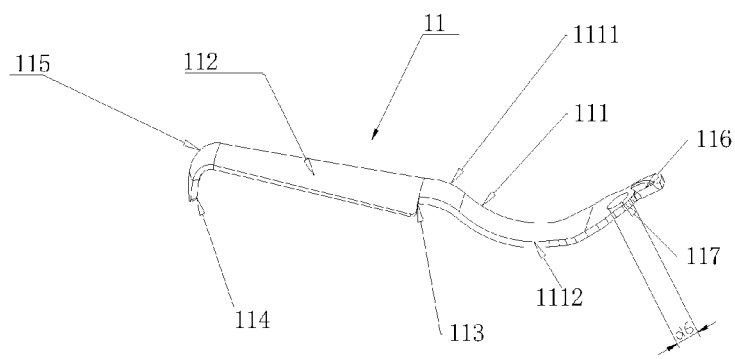
FIG. 14 is a schematic diagram showing a preferred elastic clip of the living tissue ligation device according to an embodiment of the present invention.

In this embodiment, the elastic clip is bent into the shape as shown in FIG. 14, and the elastic clip has a near end forming an arm part 111 and a outer part 112 connected to the arm part to form a connection; the diameter of the outer part 112 is larger than that of the arm part 111, to make the connection forms a stopper 113, and the stopper 113 is against the far end 120 of the end of the tightening tube 12 when the elastic clips 11 are received in the tightening tube. The end of the outer part 112 forms a claw portion 114 to bend outward, and this bending portion forms a round part 115. The second connecting hole 114 described above is formed on the arm part 111. The arm portion 111 forms a first bending portion 1111 and a second bending portion 1112.

A lug 116 is formed on one end of the elastic clip 11 of the clamp 10, and the hanging hole 122 is formed on inner wall of the tightening tube 12, when the elastic clips 11 are disengaged from the connector 322, each lug 116 is locked in the hanging hole 122 to prevent the elastic clip 11 from disengaging from tightening tube 12.

A through hole 124 is formed on the far end of the tightening tube 12 to receive the elastic clips 11, a separated member 121 is arranged on this far end and in the through hole 124, the number of the separated member is in accordance with the elastic clip, so as to separate the elastic clips one by one, also to prevent the elastic clips from disengaging from the through hole 124 of the tightening tube.

Referring to FIGS. 1-16, actions of all components are described below while the elastic clips 11 open to conduct clamping until they are released.

The inner connecting assembly 32 and the elastic clips 11 are inserted into the outer connecting assembly 31 (its near end is connected to the tightening tube 12) from its far end, then the separated member 121 is inserted into the separated hole 1210 of the tightening tube 12, which prevents the inner connecting assembly from disengaging from the outer connecting assembly 31. When the slider and shaft 321 are pushed, the elastic chips 11 move to the far end of the tightening tube 12, the second bending portion which is straightened by the tightening tube 12 returns back to its original curved state, and the outer portions of two elastic clips 11 are separated to open the clamp 10, until the bottom of the elastic clips 11 are blocked by the separated member 121 so that the elastic clips could not be pushed forwards, so far the opening process of the clamp 10 is finished. The distance L1 between the traction part of the connecting rod 313 and the contact portion of the connector 322 is obtained to be maximum, and the distance L2 between the hanging hole 122 of the tightening tube 12 and the lug 116 of the elastic clip 11 is also obtained to be maximum.

The size of each side hole of the tightening tube 12 and the connecting head 312 is larger than each wing of the connecting rod 313, to helps assembly. Owing to the push of the shaft 321, the tightening tube 12 moves forwards, and then the side holes of the tightening tube 12 and the connecting head 312 are no longer coincided with each other and are staggered, to make the wings of the connecting rod 313 lock in the side holes correspondingly, so as to prevent the tightening tube 12 disengaging from the connecting head 312 due to the movement of the elastic clips 11.

The clamp 10 is observed through the endoscopic to move towards the bleeding point and the perforation of the affected part after the clamp is open; and the physician adjusts the knob to control the endoscopic to move, or move or rotate the endoscopic directly to make the clamp 10 move in 60° or 90° towards the bleeding point, and press the affected part.

After that, the slider 22 is pulled back to drive the shaft 321 to move, the connector 322, the joint stick 323 and the elastic clips 11 to move accordingly, the distance L1 between the traction part of the connecting rod 313 and the contact portion of the connector 322 gradually reduces, and the L2 is also gradually reduces. At this moment, the elastic clips 11 are pulled back into the tightening tube 12, and two clips which are in curved state are pressed by the tightening tube 12 to be straighten and close to each other, until the stopper 113 is against the stopper face of the tightening tube 12, and the direction of the L2 changes in opposite direction, the lugs of the elastic clips 11 are beyond the hanging holes of the tightening tube 12, and two elastic clips 11 are close to each other and clamping affected part is finished. By now, the pull force does not achieve that certain releasing pull force, so that the outer connecting assembly and the inner connecting assembly do not deform, which guarantees that the clamp 10 could be opened and folded repeatedly.

If the physician observes the clamping position is not he excepts through the endoscopic, the handle 21 could be pushed, the elastic clips 11 are pushed by the shaft 321 to move out from the tightening tube 12, which is towards the far end of the tightening tube 12, and the elastic clips 11 open again, the physician could conduct another clamping action to the affected part using the elastic clips 11, and the clamping action is conducted by the physician repeatedly by the endoscopic until a ideal clamping position is obtained.

After that, the handle 21 is continued to be pulled, until the stopper 113 of the elastic clip 11 is blocked by the stopper face of the tightening tube 12, and the elastic clips 11 could not move to the near end of the tightening tube 12 anymore; at this time, the linking end face of the tightening tube 12 is against the far end face of the connecting head 312 to afford the pull force produced by the slider 22. The pull force is increased to be the certain pull force, the notch part of the connector 322 deforms or is broken, the first connecting hole of the connector 322 which is engaged with the joint stick 323 deforms, and could not engage with the joint stick 323 anymore, so that the connector 322 is separated from the joint stick 323.

Under the certain pull force, the shaft 321 drives the connector 322 to move forwards, the distance L1 between the traction part 3133 of the connecting rod 313 and the contact portion 3224 of the connector 322 becomes zero, the traction part 3133 of the connecting rod 313 is contacted with the contact portion 3224 of the connector 322. Because the minimum clearance between the thin bar of the connector 322 and the spring tube 311 is not bigger than the size d1=0.2 mm of the connecting rod 313, the connector 322 is continued to move to control the connecting rod 313 to move forwards by pulling back the handle 21 continually. The linking end face 1250 of the tightening tube 12 contacts the far end face 3124 of the connecting head 312, and the side holes which receive the connecting rod therein coincide with each other completely, and the wings 31310 of the connecting rod 313 are free from the side hole, and the wings of the connecting rod 313 are pulled out of the side holes of the connecting head 312 and the tightening tube 12, so that the connecting head 312 is separated from the tightening tube 12, therefore the clamp 10 is separated from the conveying unit 30.

So far, the elastic clips 11 which are held by the connector 322 are separated from each other due to their elasticity to form a distance k2 therebetween, and the lugs are locked in the hanging hole 122 of the tightening tube 12, so that the elastic clips 11 are not easy to be pulled out, so far the clamp 10 is released and remained in the digestive tract of the living organisms, and ligate the affected part effectively.

The description of the alternative embodiments is shown below.

Figure 17A:
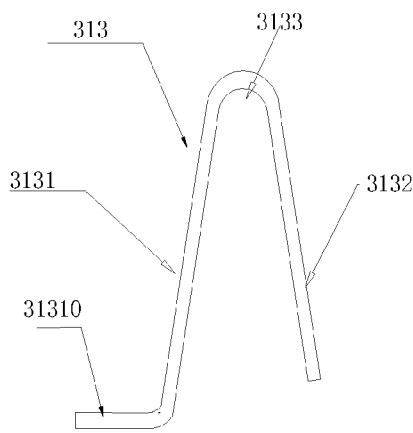
FIGS. 17a, 17b, 17c, 17d and 17e are schematic diagrams showing preferred embodiments of the connecting rod of the living tissue ligation device according to the present invention.
Figure 17B:
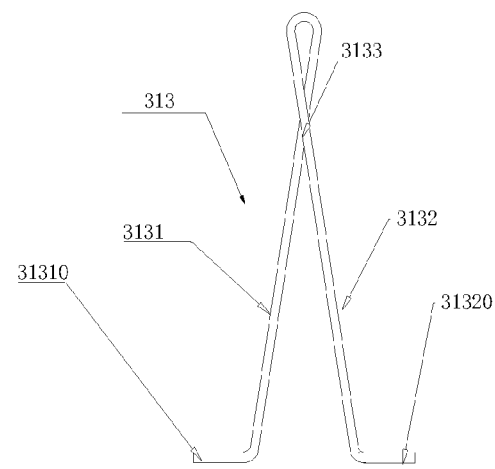
Figure 17C:
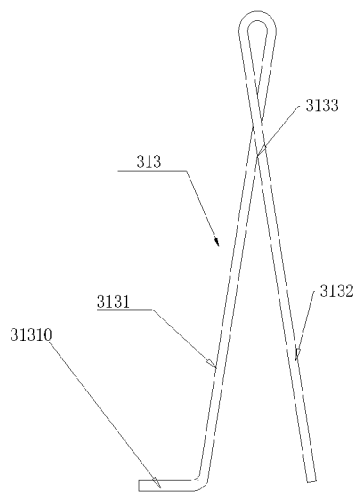
Figure 17D:
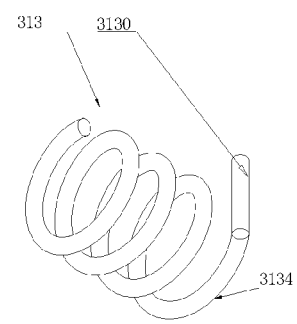
Figure 17E:
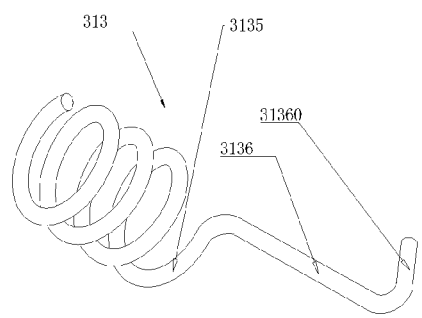

The connecting rods shown in FIGS. 17a-18c could substitute for the connecting rod 313 of the above preferred embodiment. The connecting rods 313 shown in FIGS. 17a-17e are all monolithic which is formed by bending a piece of material. Referring to FIGS. 17a-17c, the connecting rod provides two extended arms 3131 and 3132 and a traction part 3133 which is arranged between two extended arms; at least one of the extended arms has a free end having wings 31310 and 31320 formed thereon to engage with the holes or the grooves correspondingly. As shown in FIGS. 17d-17e, the traction parts 3134 and 3135 are shown, and the extensions of the traction parts 3134 and 3135 take the shape of a spiral, to be against the wall of the spring tube; one end of the traction part forms a wing 3130, or forms a extended arm 3136, and the free end of the extended arm 3136 forms a wing 31360.

Figure 18A:
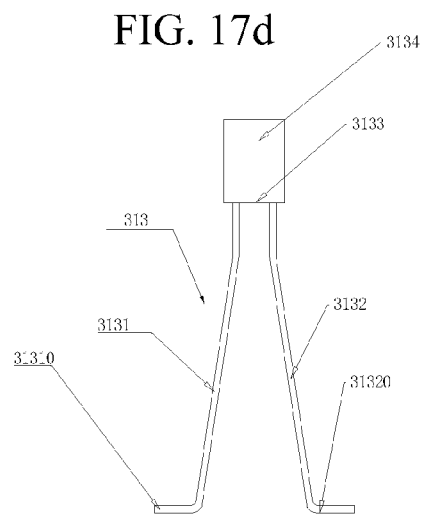
FIGS. 18a, 18b, and 18c are schematic diagrams showing preferred embodiments of the connecting rod of the living tissue ligation device according to the present invention.
Figure 18B:
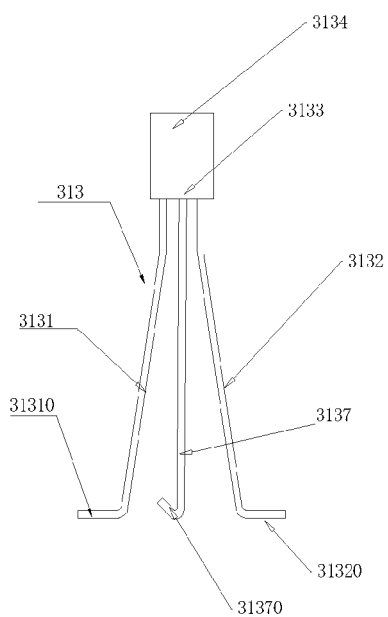
Figure 18C:
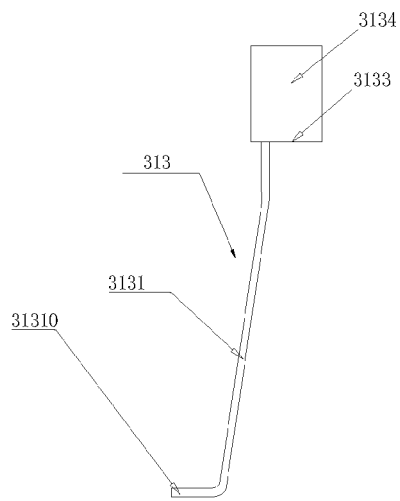

The modular connecting rods shown in FIGS. 18a-18c could substitute for the connecting rod 313 of the above preferred embodiment, and the modular connecting rod also has one or two extended arms, or three extended arms (one more extended arm 3137), each free end of each extended arm forms wings 31310, 31320 and 31370. When the number of the extended arm is more than two, it could only choose one of the extended arms to provide a wing.

Figure 19A:
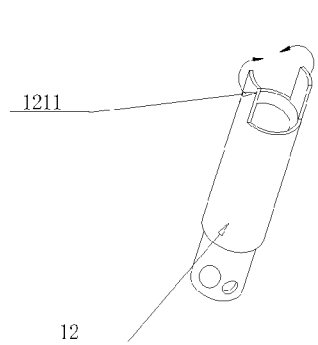
FIG. 19a is a schematic diagram showing the tightening tube of the living tissue ligation device according to the present invention, and showing the stop arm thereof.
Figure 19B:
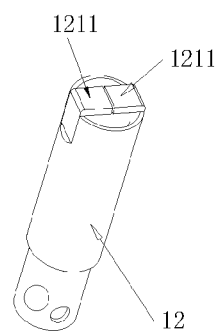
Figure 19C:
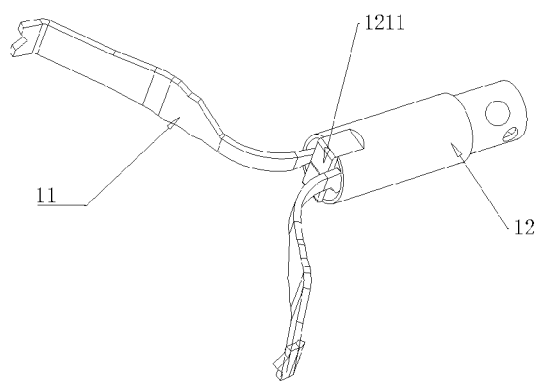
Figure 20A:
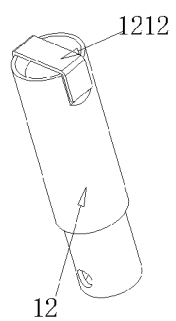
FIG. 20a is a schematic diagram showing the tightening tube of the living tissue ligation device according to another embodiment of the present invention, and showing the stop member thereof.
Figure 22A:
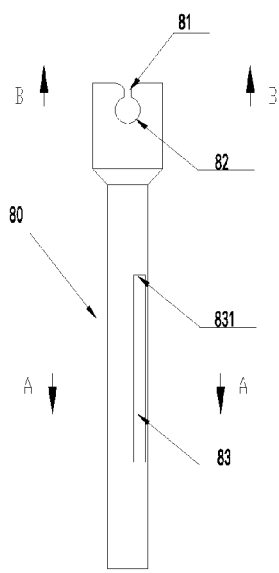
FIG. 22a is a schematic diagram showing the connector of the living tissue ligation device according to another embodiment of the present invention.
Figure 22B:
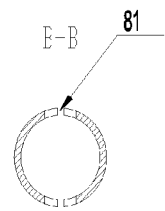
Figure 22C:
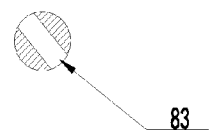
Figure 22D:
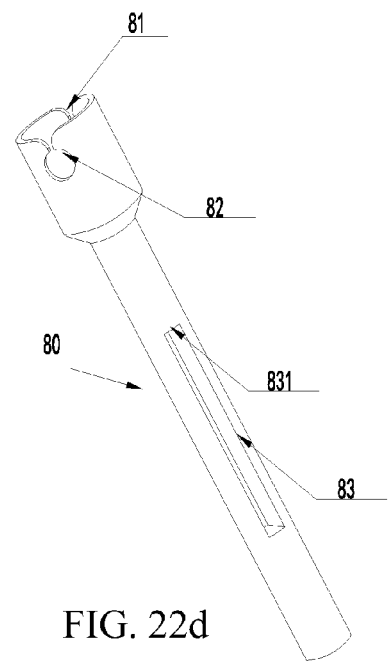

The separated member shown in FIGS. 19a-20d could substitute for the separated member 121 of the above preferred embodiment. The separated member 121 consists of two separated arms 1211 as shown in FIGS. 19a and 19b, and two separated arms are bent to form the separated member, FIG. 19c shows the using state. The separated member is assembly structure as shown in FIG. 20a, and it could be mounted on the tightening tube 12 by soldering or riveting. Two pins shown in FIG. 20b are inserted into the holes on the tightening tube 12 to form a separated member. The separated member shown in FIGS. 20c and 20d is also assembly structure, having elasticity in its axis direction, and its diameter D3 is slightly larger than the hole diameter D2 of the tightening tube 12, and one end of the separated member provides a chamfer with diameter D4 smaller than D2, the chamfer of the separated member is pressed into the hole of the tightening tube, and the separated member is contracted inward with its elasticity to insert into the hole 1210, until the separated member projects from another hole 1210; at this point, the separated member locks in the hole 1210 of the tightening tube 12 by its elasticity. The separated member could also be mounted in the hole 1210 of the tightening tube 12 by laser welding.

The connection between the tightening tube 12 and the connecting head 312 shown in above preferred embodiment could be replaced, for instance, the tightening tube 12 provides a coupling hole and side holes in the inner wall; the connecting head 312 provides a coupling part and side holes in the inner wall, the joint stick runs through four side holes to connect the tightening tube and the connecting head together.

The connector shown in FIGS. 21a-21b could substitute for the connector 322 of the above preferred embodiment. The connector 322 is made of two assembly parts, the hooks of two notch portions are in the same direction (shown in FIG. 21b), or in the opposite direction (shown in FIG. 21a). The difference between the connectors shown in FIG. 21a and FIGS. 1-16, two notch portions in FIG. 21a are integrated molding, without welding the welding holes.

The second and third embodiments of the living tissue ligation devices are described below.

The second embodiment of the present invention is shown in FIGS. 22a-22e, compared to the first embodiment, the difference lie in the connector.

Referring to FIGS. 22a-22e, the near end of the connector 80 is a cylinder, a through-groove 83 is formed on the wall of the cylinder along the axial direction, and the extended arm of the connecting rod 313 runs through the through-groove 83 to make the traction part arranged in the through-groove 83. The far end of the through-groove 83 forms a contact portion 831, and the shaft 321 is mounted in the back hole 832 of the near end of the through-groove 83 by welding. When the shaft 321 is pulled under a certain pull force, the contact portion 831 presses the traction part of the connecting rod 313, to make the wings of the connecting rod 313 disengage from the holes or grooves correspondingly.

A divider slot 81 is formed on the far end of the connector 80 along the end diameter, and a mounting hole 82 is formed at the bottom of the divider slot 81 to communicate the divider slot 81, and the connector is made of elastic material, so that the joint stick runs through the divider slot 81 to locked in the mounting hole 82. When under a certain pull force, the divider slot 81 is stretched to release the joint stick, so that the connector is disengaged from the clamp.

Figure 25:
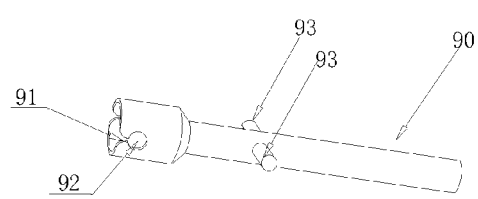
FIG. 25 is a schematic diagram showing the connector of the living tissue ligation device according to another embodiment of the present invention.

The connector 90 shown in FIG. 25 could substitute for the connector of the above preferred embodiment. As shown in FIG. 25, the contact portion is a pin 93 pierces the cylinder of the connector. The far end of the connector also provides a divider slot 91 and the mounting hole 92, other structure is similar to the connector 90 shown above.

Figure 22E:
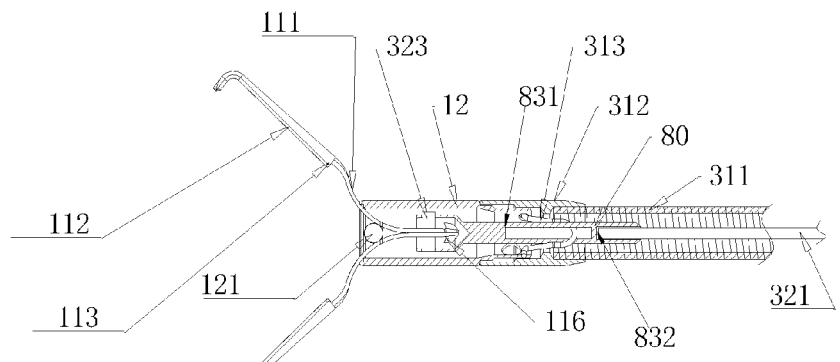
FIG. 22e is a use state diagram showing the connector of FIG. 22a, and showing the clip, the connector, the connecting rod, the connecting head, the spring tube, and the shaft, etc.

In above embodiment, referring to FIG. 22e, a notch is formed below the through-groove 83 of the near end of the connector 80 to engage with the lug 116, which is a support to the lug 116 to apply force on the lug 116.

Figure 23:
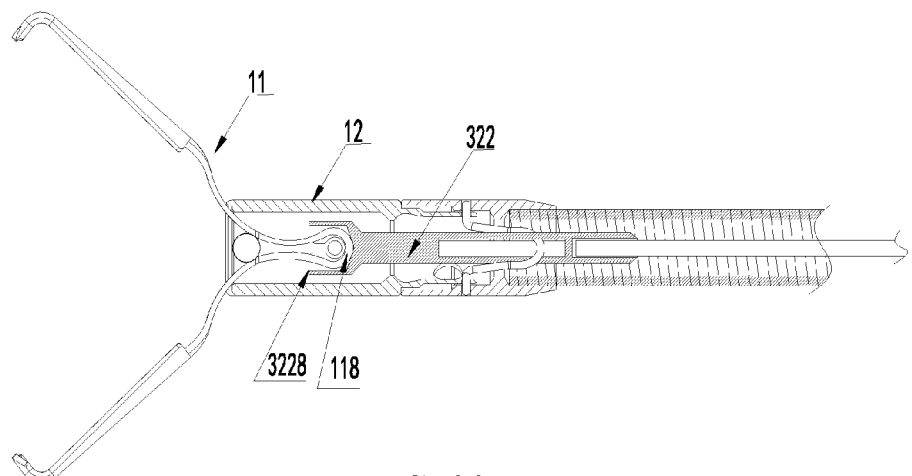
FIG. 23 is a schematic diagram showing the living tissue ligation device according to another embodiment of the present invention.

The third embodiment of the present invention as shown in FIGS. 23 and 24, which is similar to the second embodiment, the difference is that the clamp 40 is from assembly structure to one unitary structure. A curved base 118 is formed at the bottom of the elastic clips, a concave 3228 is formed on the far end of the connector to engage with the curved base 118, and the connector is made of elastic material. The curved base 118 could be received in the concave 3228, and the joint stick 328 is locked in the concave 3228 correspondingly, to make the elastic clips connect to the connector.

When the handle is pulled to make the stopper of the elastic clip contact with the stopper face of the tightening tube, and then the connector is pulled, the concave 3228 of the connector is deformed to make the connector separate from the joint stick, and the curved base 118 of the elastic clip is disengaged from the concave 3228 to cause friction between the tightening tube and the curved base, and finally stuck in the tightening tube, further to prevent the movement between the elastic clips and the tightening tube. Then the contact portion of the connector is against the traction part of the connecting rod, the connector is continued to be pulled, the connector drives the connecting rod to move, so as to drag the wings of the connecting rod from the side holes of the tightening tube and the connecting head, and the clamp is separated from the conveying unit.

All components mentioned above and the above three embodiment could be replaced.

All the above are the preferred embodiments of the present invention. It is to be understood that, for one skilled in the art, the invention is intended to cover various modifications and equivalent arrangements included within the principle of the invention.

Symbols in the drawings:
 Clamp 10:
  elastic clips 11: arm part 111, outer part 112, stopper 113, claw portion 114, round part 115, lug 116, second connecting hole 117;
  tightening tube 12: separated member 121, separated hole 1210, hanging hole 122, separated arms 1211, side hole 123, separated member 1212, through hole 124, separated member 1213, linking part 125, separated member 1214, linking end face 1250, far end 120;
  operating unit 20: handle 21, slider 22, guiding bar 23;
  conveying unit 30:
  outer connecting assembly 31: spring tube 311, linking hole 3122, side hole 3121, connecting head 312, far end face 3124, chamfer 3123, connecting rod 313, coupling hole 3126, separated step 3125, extended arms 3131 and 3132, wing 31310, 31320, 3130 and 31360, traction part 3133, extended arm 3136, traction part 3134 and 3135;
  inner connecting assembly 32: thin end 3210, flatten end 3211, shaft 321, thin bar 3221, notch part 3222, connector 322, notch portion 32221 and 32222, joint stick 323, first connecting hole 3223, welding hole 301, contact portion 3224, second welding hole 302;
  connector 80 and 90: divider slot 81 and 91, mounting hole 82 and 92, through-groove 83, contact portion 831, back hole 832, pin 93, curved base 118, concave 3228.

What is claimed is:
1. A living tissue ligation device, characterized by comprising a clamp, an operating unit, and a conveying unit; the clamp comprising elastic clips and a tightening tube to receive the elastic clips therein; the operating unit comprising a handle and a slider sliding on the handle; and the conveying unit comprising an outer connecting assembly and an inner connecting assembly;
wherein the outer connecting assembly comprises a spring tube, a connecting head, and a connecting rod; one end of the spring tube is connected to the handle, the other end of the spring tube is connected to one end of the connecting head, the other end of the connecting head is coupled to one end of the tightening tube via the connecting rod, and a connecting part of the connecting rod is disengaged from holes or grooves under a certain pull force, to make the connecting head disengage from the tightening tube;
the inner connecting assembly which runs through the outer connecting assembly comprises a shaft, a connector and a joint stick; one end of the shaft is connected to the slider of the operating unit by a guiding bar, and the shaft is pulled by the slider; the other end of the shaft is connected to a near end of the connector; a far end of the connector is connected to one end of the elastic clip via the joint stick, and the far end of the connector is deformed under a certain pull force, to disengage from the end of the elastic clip;

the connecting rod is pulled by the connector, and the connecting part of the connecting rod is disengaged from the holes or the grooves under the pull force;

wherein the connecting rod comprises at least one extended arm and a traction part which is connected to the bottom of the extended arm, wings are formed on the top of the extended arm, and the wings are configured to match the holes or the grooves of the connecting head and the tightening tube, and insert into the holes or the grooves correspondingly to connect the connecting head and the tightening tube together, and the wings are deformed under a certain pull force to disengage from the holes or the grooves;

the connector comprises a thin bar and a notch part connected to one end of the thin bar, the other end of the thin bar is connected to one end of the shaft, a free end of the notch part forms hooks, which form a first connecting hole to engage with the joint stick, a second connecting hole is formed at the bottom of the elastic clip to engage with the joint stick, and the joint stick runs through the first connecting hole and the second connecting hole to make the elastic clip connect to the connector; the hooks are deformed under a certain pull force to disengage from the elastic clip.

2. The living tissue ligation device according to claim 1, characterized in that the connecting rod which is formed by bending a single piece of material, comprises two extended arms and the traction part which is arranged between two extended arms; at least one said extended arm has a free end having a wing formed thereon to engage with the hole or the groove correspondingly.

3. The living tissue ligation device according to claim 1, characterized in that the connecting rod which is formed by bending a single piece of material, comprises at least one extended arm and the traction part which is connected to the bottom of the extended arm;

the extended arm has a free end having a wing formed thereon to engage with the hole or the groove correspondingly.

4. The living tissue ligation device according to claim 1, characterized in that the notch part comprises two notch portions, each notch portion has a free end to form a hook, which forms the first connecting hole to engage with the joint stick.

5. The living tissue ligation device according to claim 1, characterized in that the thickness of the end of the thin bar is greater than the diameter of the shaft, and the thin bar has a contact portion at the point where the thin bar meets the shaft, when the shaft is pulled under a certain pull force, the contact portion is pressed against the traction part of the connecting rod to make the wings of the connecting rod disengage from the holes or grooves.

6. The living tissue ligation device according to claim 1, characterized in that the elastic clip has an arm part and an outer part connected to the arm part to form a connection; the diameter of the outer part is larger than that of the arm part to make the connection form a stopper, and the stopper is against one end of the tightening tube when the elastic clips are received in the tightening tube in a certain position.

7. The living tissue ligation device according to claim 6, characterized in that a lug is formed on one end of the elastic clip; hanging holes are formed on an inner wall of the tightening tube, when the elastic clips are disengaged from the connector, each lug is locked in the hanging hole to prevent the elastic clip from disengaging from the tightening tube.

8. The living tissue ligation device according to claim 1, characterized in that a curved base is formed at the bottom of the elastic clip of the clamp, a concave is formed on one end of the connector to match the curved base, with the curved base being received in the concave, and the joint stick being locked in the concave correspondingly, and the connector is consists of elastic material, and the concave is deformed under a certain pull force to disengage from the curved base and the joint stick.

9. The living tissue ligation device according to claim 1, characterized in that a separated member is arranged on one end of the tightening tube to separate the elastic clips and prevent the elastic clips from disengaging from the tightening tube.

10. The living tissue ligation device according to claim 1, characterized in that the joint stick is a pin.

11. The living tissue ligation device according to claim 1, characterized in that the joint stick consists of metal material or high strength nonmetallic material, so that the joint stick is without deformation when the connector is under a certain pull force.

12. A living tissue ligation device, characterized by comprising a clamp, an operating unit, and a conveying unit; the clamp comprising elastic clips and a tightening tube to receive the elastic clips therein; the operating unit comprising a handle and a slider sliding on the handle; and the conveying unit comprising an outer connecting assembly and an inner connecting assembly;

wherein the outer connecting assembly comprises a spring tube, a connecting head, and a connecting rod; one end of the spring tube is connected to the handle, the other end of the spring tube is connected to one end of the connecting head, the other end of the connecting head is coupled to one end of the tightening tube via the connecting rod, and a connecting part of the connecting rod is disengaged from holes or grooves under a certain pull force, to make the connecting head disengage from the tightening tube;

the inner connecting assembly which runs through the outer connecting assembly comprises a shaft, a connector and a joint stick; one end of the shaft is connected to the slider of the operating unit by a guiding bar, and the shaft is pulled by the slider; the other end of the shaft is connected to a near end of the connector; a far end of the connector is connected to one end of the elastic clip via the joint stick, and the far end of the connector is deformed under a certain pull force, to disengage from the end of the elastic clip;

the connecting rod is pulled by the connector, and the connecting part of the connecting rod is disengaged from the holes or the grooves under the pull force;

wherein the connecting rod comprises at least one extended arm and a traction part which is connected to the bottom of the extended arm, wings are formed on the top of the extended arm, and the wings are configured to match the holes or the grooves of the connecting head and the tightening tube, and insert into the holes or the grooves to connect the connecting head and the tightening tube together, and the wings are deformed under a certain pull force to disengage from the holes or the grooves;

one end of the connector is a cylinder, a through-groove is formed on the wall of the cylinder along the axial direction, and the extended arm of the connecting rod runs through the through-groove to make the traction part arranged in the through-groove; a contact portion is formed on one end of the through-groove, and when the shaft is pulled under a certain pull force, the contact portion is pressed against the traction part to make the wings of the connecting rod disengage from the holes or grooves.

13. The living tissue ligation device according to claim 12, characterized in that the elastic clip has an arm part and an outer part connected to the arm part to form a connection; the diameter of the outer part is larger than that of the arm part to make the connection form a stopper, and the stopper is against one end of the tightening tube when the elastic clips are received in the tightening tube in a certain position.

14. The living tissue ligation device according to claim 13, characterized in that a lug is formed on one end of the elastic clip; hanging holes are formed on an inner wall of the tightening tube, when the elastic clips are disengaged from the connector, each lug is locked in the hanging hole to prevent the elastic clip from disengaging from the tightening tube.

15. The living tissue ligation device according to claim 12, characterized in that a curved base is formed at the bottom of the elastic clip of the clamp, a concave is formed on one end of the connector to match the curved base, with the curved base being received in the concave, and the joint stick being locked in the concave correspondingly, and the connector consists of elastic material, and the concave is deformed under a certain pull force to disengage from the curved base and the joint stick.

16. The living tissue ligation device according to claim 12, characterized in that a separated member is arranged on one end of the tightening tube to separate the elastic clips and prevent the elastic clips from disengaging from the tightening tube.

\* \* \* \* \*